US00PP13539P2

(12) United States Plant Patent
Sakazaki

(10) Patent No.: US PP13,539 P2
(45) Date of Patent: Feb. 4, 2003

(54) PETUNIA PLANT NAMED 'CONSTRAW'

(75) Inventor: Ushio Sakazaki, Hikone (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 09/996,375

(22) Filed: Nov. 30, 2001

(51) Int. Cl.[7] ..... A01H 5/00
(52) U.S. Cl. ..... Plt./356
(58) Field of Search ..... Plt./356

(56) References Cited

U.S. PATENT DOCUMENTS

PP10,309 P * 3/1998 Adolph ..... Plt./356

PP10,904 P * 5/1999 Hansson ..... Plt./356

OTHER PUBLICATIONS

UPOV–ROM GTITM Computer Database, 2002/03, GTI Jouve Retrieval Software, citation for 'Constraw'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Petunia plant named 'Constraw', characterized by its outwardly spreading and uniform plant habit; freely branching habit; small rounded leaves; numerous small single flowers that are purple in color with darker purple-colored venation; and good garden performance.

1 Drawing Sheet

BOTANICAL CLASSIFICATION/CULTIVAR DESIGNATION

*Petunia×hybrida* cultivar Constraw.

BACKGROUND OF THE INVENTION

The present Invention relates to a new and distinct cultivar of Petunia plant, botanically known as *Petunia×hybrida*, and hereinafter referred to by the cultivar name Constraw.

The new Petunia is a product of a planned breeding program conducted by the Inventor in Shiga Prefecture, Japan. The objective of the breeding program is to create new Petunias with numerous small flowers with attractive flower colors.

The new Petunia originated from a cross made by the Inventor on Dec. 25, 1998 of the Petunia cultivar Fantasy Crystal Red, not patented, as the female, or seed parent, with an unidentified selection of Petunia, not patented, as the male, or pollen parent. The new Petunia was selected as a single plant from the resulting progeny by the Inventor on Sep. 25, 1999, in Shiga Prefecture, Japan, on the basis of its small and numerous purple-colored flowers with darker purple-colored venation.

Asexual reproduction of the new cultivar by terminal vegetative cuttings taken in Gensingen, Germany has shown that the unique features of this new Petunia are stable and reproduced true to type in successive generations.

SUMMARY OF THE INVENTION

Plants of the cultivar Constraw have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Constraw'. These characteristics in combination distinguish 'Constraw' as a new and distinct cultivar:

1. Outwardly spreading and uniform plant habit.
2. Freely branching habit.
3. Small rounded leaves.
4. Numerous small single flowers that are purple in color with darker purple-colored venation.
5. Good garden performance.

Plants of the new Petunia differ from plants of the female parent, the cultivar Fantasy Crystal Red, in the following characteristics:

1. Plants of the new Petunia are more outwardly spreading and not as upright as plants of the female parent.
2. Plants of the new Petunia are more vigorous than plants of the female parent.
3. Plants of the new Petunia have better garden performance than plants of the female parent.

Plants of the new Petunia differ from plants of the male parent, the unidentified Petunia selection, in the following characteristics:

1. Plants of the new Petunia are more vigorous than plants of the male parent.
2. Plants of the new Petunia have larger flowers than plants of the male parent.
3. Plants of the new Petunia flower for a longer period of time than plants of the male parent.

Plants of the new Petunia are similar in flower color to the cultivar Revolution Marrose, disclosed in U.S. Plant Pat No. 10,904; however in side-by-side comparisons conducted in Gensingen, Germany, plants of the new Petunia had smaller flowers than plants of the cultivar Revolution Marrose.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of three typical flowering plants of 'Constraw' grown in a 20-cm container.

The photograph at the bottom of the sheet comprises a close-up view of a typical flower bud, a typical opening flower, upper surfaces of typical fully opened and faded flowers, and lower and upper surfaces of typical fully expanded leaves of 'Constraw'.

DETAILED BOTANICAL DESCRIPTION

The aforementioned photographs and following observations and measurements describe plants grown in Bonsall, Calif., in an outdoor nursery during the late spring and early summer under full sun conditions with day temperatures ranging from 18 to about 35° C. and night temperatures ranging from 4 to 18° C. After planting rooted cuttings, plants were grown for about nine weeks in 20-cm containers with three plants per container. Color references are made to The Royal Horticultural Society Colour Chart, 1995 edition, except where general terms of ordinary dictionary significance are used.

Botanical classification: *Petunia×hybrida* cultivar Constraw.

Parentage:

*Female parent.*—*Petunia×hybrida* cultivar Fantasy Crystal Red, not patented.

*Male parent.*—Unidentified *Petunia×hybrida* selection, not patented.

Progagation:

*Type cutting.*—Terminal vegetative cuttings.

*Time to initiate roots, summer and winter.*—About 15 days at 20 to 22° C.

*Time to develop roots, summer and winter.*—About 20 days at 18 to 22° C.

*Root description.*—Fine; white, close to 155D, in color.

*Rooting habit.*—Freely branching.

Plant description:

*Form.*—Annual flowering plant; indeterminate; initially upright, then outwardly spreading and trailing; uniform. Freely branching habit with about eight lateral branches per plant.

*Usage.*—Appropriate for hanging baskets, window boxes, patio containers and landscape applications.

*Plant height.*—About 14 cm.

*Plant diameter.*—Individual plant: About 22.5 cm. All three plants: About 50 cm.

*Vigor.*—Vigorous.

*Lateral branches.*—Length: About 24 cm. Diameter: About 2 mm. Internode length: About 1.2 to 1.5 cm. Texture: Pubescent. Color: 144B.

*Foliage description.*—Arrangement: Alternate before flowering; opposite after flowers develop; simple. Quantity per lateral branch: About 20. Length: About 3.7 cm. Width: About 2.5 cm. Shape: Elliptic, rounded. Apex: Broadly acute. Base: Attenuate. Margin: Entire. Texture: Upper and lower surfaces, pubescent and glandular. Venation pattern: Pinnate, arcuate. Color: Developing and fully expanded leaves, upper surface: 137B. Developing and fully expanded leaves, lower surface: 137C. Venation, upper surface: 144B. Venation, lower surface: 144D. Petiole length: About 1.5 cm. Petiole diameter: About 2.5 mm. Petiole color: 144D.

Flower description:

*Flower type and habit.*—Single salverform flowers; flowers face mostly upward or outward; axillary. Very freely flowering habit, about five flowers and flower buds per lateral branch at one time.

*Natural flowering season.*—Long day responsive; long flowering period, spring until frost in the autumn; flowering continuous during this period. Plants start flowering about three weeks after planting rooted cuttings. Flowers persistent.

*Flower longevity on the plant.*—About three to four days.

*Fragrance.*—Not detected.

*Flower size.*—Diameter: About 3.75 cm. Tube length: About 2.4 cm. Throat diameter, distal end: About 6 mm. Tube diameter, proximal end: About 3 mm.

*Flower buds* (*showing color*).—Length: About 2 cm. Diameter: At apex, about 7.5 mm; at base, about 5 mm. Shape: Elongated oblong with ruffled apices. Color: Towards apex, 195B; towards base, 186B.

*Corolla.*—Quantity/arrangement: Five fused petals in a single whorl, funnelform. Petal length from throat: About 1.7 cm. Petal width: About 1.8 cm. Petal shape: Roughly spatulate or fan-shaped. Petal apex: Broadly acute. Petal margin: Entire. Petal texture: Smooth, velvety. Color: Petal, upper surface, when opening: 71D. Petal, lower surface, when opening: 75C. Petal, upper surface, fully opened: 78C; color fading to 78D with subsequent development. Petal, lower surface, fully opened: 75C. Flower throat (inside): 75A. Flower tub (outside): 145B to 145C. Venation, upper petal surface: 74A. Venation, lower petal surface: 145C. Venation, throat: 77B. Venation, tube: 145B.

*Sepals.*—Arrangement/appearance: Single whorl of five sepals fused at base, star-shaped. Length: About 1 cm. Width: About 2 mm. Shape: Strap-like; elongate. Apex: Rounded. Margin: Entire. Texture, both surfaces: Pubescent, glandular. Color, upper and lower surfaces: 138A.

*Peduncles.*—Length: About 2.8 cm. Width: About 1 mm. Angle: About 45° from the stem. Strength: Moderately strong. Texture: Pubescent. Color: 144A.

*Reproductive organs.*—Stamens: Quantity per flower: About five. Anther shape: Ovoid. Anther size: About 1.5 mm by 1.5 mm. Anther color: 155A. Pollen amount: Scarce. Pollen color: 156B. Pistils: Quantity per flower: One. Pistil length: About 1.9 cm. Style length: About 1.5 cm. Style color: 144D. Stigma shape: Bi-lobed. Stigma color: 144B. Ovary color: 144B to 144C.

*Seed/fruit.*—Seed and/or fruit production has not been observed to date.

Disease/pest resistance: Plants of the new Petunia have not been noted to be resistant to pathogens or pests common to Petunia.

Garden performance: Plants of the new Petunia have been observed to have good garden performance. Plants of the new Petunia have been noted to tolerate temperatures from 0 to 35° C. and have excellent tolerance to rain and wind.

It is claimed:

1. A new and distinct cultivar of Petunia plant named 'Constraw', as illustrated and described.

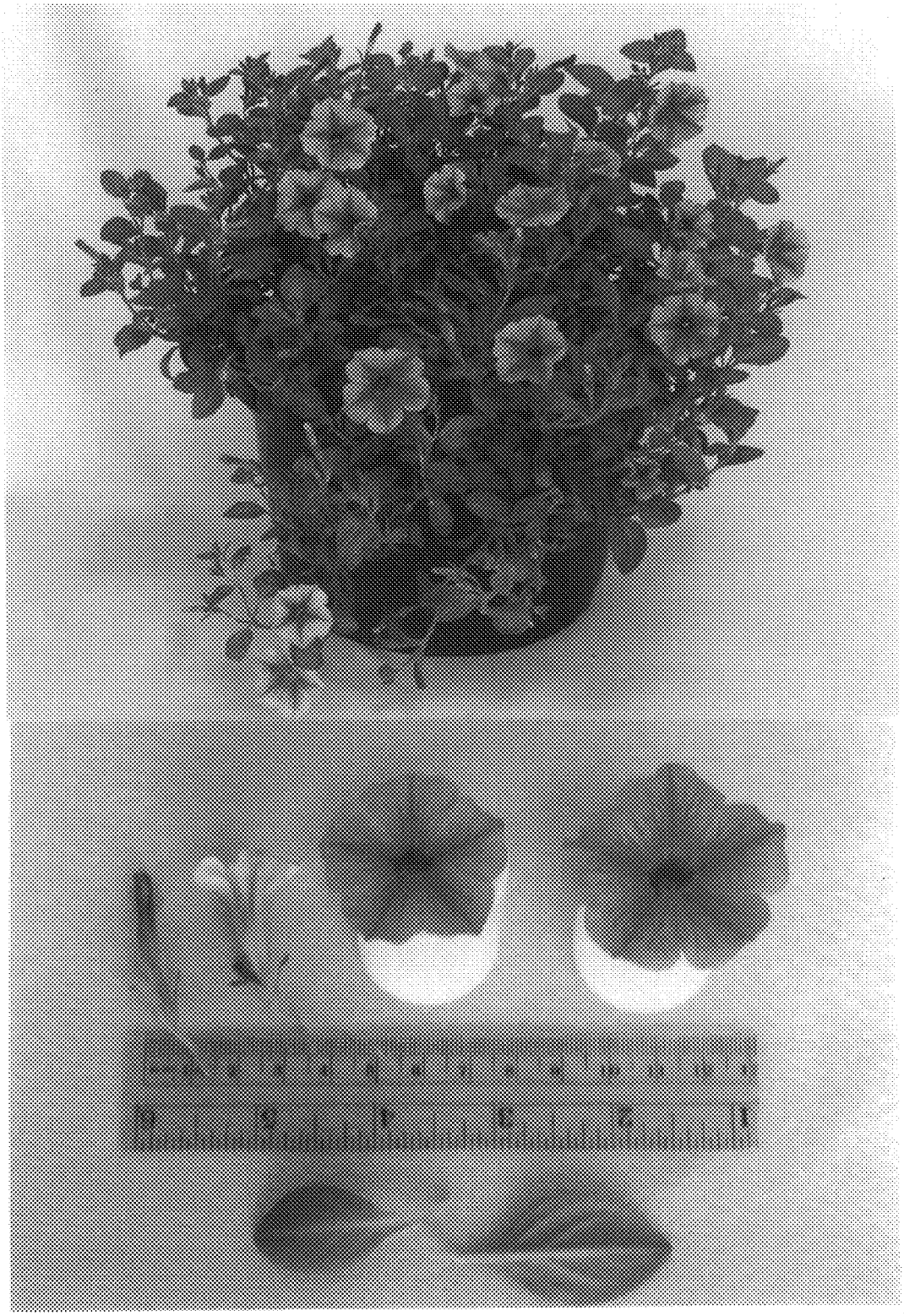

* * * * *